United States Patent [19]

Thompson et al.

[11] 4,115,388

[45] Sep. 19, 1978

[54] 3'-OXYGENATED DERIVATIVES OF 4'-DEOXY VLB "A" AND "B" AND RELATED 1-FORMYL COMPOUNDS

[75] Inventors: Gerald L. Thompson; Gloria C. Paschal, both of Indianapolis, Ind.

[73] Assignee: Eli Lilly and Company, Indianapolis, Ind.

[21] Appl. No.: 782,644

[22] Filed: Mar. 30, 1977

[51] Int. Cl.$^2$ .................................... C07D 519/04
[52] U.S. Cl. ............................................ 260/287 B
[58] Field of Search ................................ 260/287 B

[56] References Cited

U.S. PATENT DOCUMENTS

| 3,352,868 | 4/1964 | Neuss et al. ............... 260/287 B |
| 3,887,565 | 6/1975 | Jones et al. ................ 260/287 B |
| 3,944,554 | 3/1976 | Tafur ......................... 260/287 B |

OTHER PUBLICATIONS

Neuss et al., "Tetrahedron Letters," 811, (1967).
Ibid., 783 (1968).

*Primary Examiner*—Donald G. Daus
*Assistant Examiner*—David E. Wheeler
*Attorney, Agent, or Firm*—James L. Rowe; Arthur R. Whale

[57] ABSTRACT

3'-hydroxy and 3'-keto derivatives of 4'-deoxy VLB (deoxy VLB "A"), 4'-deoxyleurosidine (deoxy VLB "B"), 4'-deoxyvincristine and 4'-deoxy-1-desmethyl-1-formylleurosidine and related 4-desacetyl and C-3 carboxamide derivatives, useful as anti-tumor agents in mammals.

8 Claims, No Drawings

3'-OXYGENATED DERIVATIVES OF 4'-DEOXY VLB "A" AND "B" AND RELATED 1-FORMYL COMPOUNDS

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leurosidine (vinrosidine) and leurocristine (VCR or vincristine) (both in U.S. Pat. No. 3,205,220), deoxy VLB "A" and "B", [*Tetrahedron Letters,* 783 (1968)] (desacetyl leurosine hydrazide is also disclosed therein), 4-desacetoxyvinblastine (U.S. Pat. No. 3,954,773); 4-desacetoxy-3'-hydroxyvinblastine (U.S. Pat. No. 3,944,554); leurocolombine (U.S. Pat. No. 3,890,325), leuroformine (N-formylleurosine, see Belgian Pat. No. 811,110) and vincadioline (U.S. Pat. No. 3,887,565). Two of these alkaloids, VLB and leurocristine, are now marketed as drugs for the treatment of malignancies in humans, particularly the leukemias and related diseases.

The dimeric indole-dihydroindole alkaloids obtainable from *Vinca rosea* can be represented by the formula:

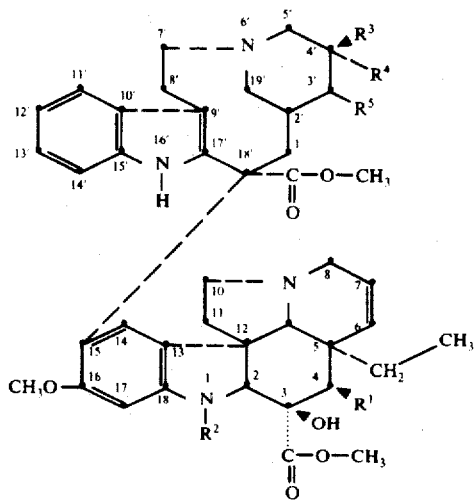

In the above formula where $R^1$ is acetoxy, $R^2$ is methyl, $R^3$ is hydroxyl, $R^4$ is ethyl and $R^5$ is H, VLB is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl and $R^5$ is H, leurosidine is represented; where $R^1$ is acetoxy, $R^2$ is methyl, $R^3$ and $R^5$ are H and $R^4$ is ethyl, deoxy VLB "A" is represented; where $R^1$, $R^2$ and $R^5$ are the same as in deoxy VLB "A" but $R^3$ is ethyl and $R^4$ is hydrogen, deoxy VLB "B" is represented; and where $R^1$ is acetoxy, $R^2$ is methyl, $R^3$ is ethyl and $R^4$ and $R^5$ taken together form an α-epoxide ring, leurosine is represented.

Leuroformine has the same structure as leurosine except that $R^2$ is formyl, not methyl. Leurocolombine and vincadioline are 2'-hydroxy VLB and 3'-hydroxy respectively. 4-Desacetoxy VLB has the same structure as VLB except that $R^1$ is H rather than acetoxy; 3'-hydroxy-4-desacetoxy VLB can also be called 4-desacetoxy vincadioline.

It should be noted that Neuss, Gorman, Cone, and Huckstep, *Tetrahedron Letters,* 783 (1968) treated leurosine with Raney nickel in absolute ethanol to produce predominately deoxy VLB "B" with minor amounts of deoxy VLB "A", i.e., the hydrogenation removed the epoxide oxygen from leurosine and produced some racemization. Furthermore, Neuss, Huckstep, and Cone reported in *Tetrahedron Letters,* 811 (1967) erroneously that leurosidine was 3'-hydroxy deoxy VLB "B" (β-ethyl group at C-4'). Wenkert, Hagaman, Lal, Gutowski, Miller and Neuss, Helv. Chim. Acta, 58, 1560 (1975) have now determined that leurosidine is a 4'-hydroxy compound isomeric with VLB (α-hydroxy-β-ethyl at C-4' rather than β-hydroxy-α-ethyl as in VLB) —see also N. Langlais and P. Potier, *Tetrahedron Letters,* 1099 (1976) who have prepared leurosidine by partial synthesis.

Chemical modification of the Vinca alkaloids has been rather limited. In the first place, the molecular structures involved are extremely complex and chemical reactions which affect a specific function of the molecule are difficult to develop. Secondly, alkaloids lacking desirable chemo-therapeutic properties have been recovered from *Vinca rosea* fractions, and a determination of their structures has led to the conclusion that these compounds are closely related to the active alkaloids. Thus, anti-neoplastic activity seems to be limited to very specific structures, and the chances of obtaining more active drugs by modification of these structures would seem to be correspondingly slight. Among the successful modifications of physiologically-active alkaloids has been the preparation of dihydro VLB (U.S. Pat. No. 3,352,868) and the replacement of the acetyl group at C-4 (carbon no. 4 of the VLB ring system-see the numbered structure below) with higher alkanoyl group or with unrelated acyl groups. (See U.S. Pat. No. 3,392,173.) Several of these derivatives are capable of prolonging the life of mice innoculated with P1534 leukemia. One of the derivatives in which a chloracetyl group replaced the C-4 acetyl group of VLB was also a useful intermediate for the preparation of structurally modified VLB compounds in which an N,N-dialkylglycl group replaced the C-4 -acetyl group of VLB (see U.S. Pat. No. 3,387,001). An intermediate compound, namely 4-desacetyl VLB, was produced during the chemical reactions leading to these latter derivatives. This intermediate, in which the C-4 acyl group was lacking, leaving an unesterified hydroxy group, has been reported to be a toxic material having little in vivo chemotherapeutic activity against the P1534 murine leukemia system by Hargrove, Lloydia, 27, 340 (1964).

One of the more recent, and successful, chemical modifications of the dimeric indole-dihydroindole alkaloids from *vinca* has been the replacement of the C-3 ester function with an amide or hydrazide function usually with the concomitant loss of the acetyl at C-4 (which group can be replaced). Amides of the alkaloids of VLB, leurosidine, vincristine, deoxy VLB "A" and "B", leurocolombine, vincadioline, 4-desacetoxy VLB, 3'-hydroxy-4-desacetoxy VLB, etc. are disclosed in Belgian Pat. No. 837,390.

Two of the above alkaloids, VLB and vincristine are now marketed for the treatment of malignancies in humans. Of these two, vincristine is the most useful, and the least available. Recently, Jovanovics et al., U.S. Pat.

No. 3,899,493, have developed an oxidative method for converting the relatively more abundant VLB into vincristine by chromic acid oxidation at low ($-60°$ C.) temperatures. There are other relatively abundant alkaloids such as leurosine in the dimeric indole-dihydroindole fraction from *vinca* and it would be desirable to convert these directly or indirectly to vincristine or to a drug of comparable oncolytic activity.

It is known that leurosine can be converted to deoxy VLB "B" (along with varying amounts of deoxy VLB "A") by treatment with Raney nickel in refluxing absolute ethanol— see Neuss, Gorman, Cone and Huckstep, *Tetrahedron Letters*, 783-7 (1968).

It is an object of this invention to convert the relatively abundant alkaloid leurosine to other oncolytically active structures not heretofore attainable.

SUMMARY OF THE INVENTION

In fulfillment of the above and other objects, this invention provides compounds represented by the following formula:

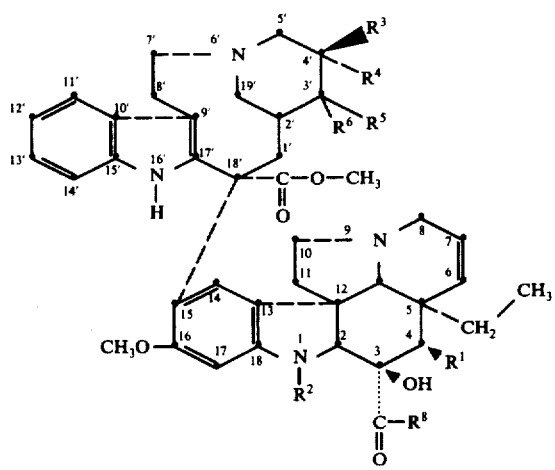

wherein $R^1$ is OH or acetoxy; $R^2$ is $CH_3$ or CHO, one of $R^3$ and $R^4$ is hydrogen and the other is ethyl; when taken singly, one of $R^5$ and $R^6$ is hydrogen and the other is $OR^7$ and, when taken together, are oxygen; wherein $R^7$ is hydrogen or

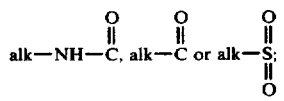

$R^8$ is $OCH_3$, $NH_2$, $NH-CH_3$, $NH-NH_2$, $N_3$, $NH-CH_2-CH_2-OH$, $NH-CH_2-CH_2-Oalk$, $NH-CH_2-CH_2-SH$ or $NH-CH_2-CH_2-S-alk$; and wherein alk is ($C_1-C_3$) alkyl, such that when $R^1$ is acetoxy, $R^8$ is $OCH_3$, $NH_2$, $NH-CH_3$, $NH-CH_2-CH_2-Oalk$ or $NH-CH_2-CH_2-S-alk$.

The term "alk" is used herein is defined as ($C_1-C_3$) alkyl and includes methyl, ethyl, n-propyl and isopropyl.

In the above formula, when $R^2$ is methyl, $R^3$ is H and $R^4$ is ethyl, the compounds are derivatives of 4-deoxy VLB (also called deoxy VLB "A"); when $R^2$ is methyl, $R^3$ is ethyl and $R^4$ is H, the compounds are derivatives of 4'-deoxyleurosidine (also called deoxy VLB "B"); when $R^2$ is formyl, $R^3$ is H and $R^4$ is ethyl, the compounds are derivatives of 4'-deoxyvincristine; and when $R^2$ is formyl, $R^3$ is ethyl and $R^4$ is H, the compounds are derivatives of 4'-deoxy-1-formylleurosidine. Compounds in which $R^1$ is OH are referred to as 4-desacetylderivatives. In the parent alkaloids themselves such as 4'-deoxy VLB, 4'-deoxy vincristine, etc. $R^8$ is $OCH_3$. In such compounds, when the $OCH_3$ group is replaced by an amide group, i.e., when $R^8$ is $NH_2$ or $NH-CH_3$, for example, the resulting compound is designated as a C-3 carboxamide or as an N-methyl C-3 carboxamide. In each of the above names, the term "C-3 descarbomethoxy" should be understood, but will not be included for sake of brevity. Likewise, in the 4'-deoxy-1-formylleurosidines, it will be understood that the 1-methyl group of leurosidine has been replaced by a formyl group and that the "1-desmethyl" term has been omitted to simplify the nomenclature.

Non-toxic acids useful for forming pharmaceutically-acceptable acid addition salts of the compounds of this invention include salts derived from inorganic acids such as: hydrochloric acid, nitric acid, phosphoric acid, sulfuric acid, hydrobromic acid, hydriodic acid, nitrous acid, phosphorus acid and the like, as well as salts of non-toxic organic acids including aliphatic mono and dicarboxylic acids, phenyl-substituted alkanoic acids hydroxy alkanoic and alkandioic acids, aromatic acids, aliphatic and aromatic sulfonic acids, etc. Such pharmaceutically-acceptable salts thus include the sulfate pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptoanate, propiolate, oxalate, malonate, succinate, suberate, sebacate, fumarate, maleate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

The compounds of this invention are prepared by treatment of leurosine with Raney nickel in absolute alcohol following the procedure of Neuss, Gorman, Cone, and Huckstep, *Tetrahedron Letters*, 783, (1968). The procedure yields, in addition to deoxy VLB "A" and deoxy VLB "B" (both found by those authors), a new material identified as 3'α-hydroxy-4'-deoxy VLB "B" or preferably 3'α-hydroxy-4'-deoxyleurosidine. Oxidation of this compound yields 3'-keto-4'-deoxyleurosidine, a key intermediate. Reduction of the 3'-ketone with sodium borohydride yields 3'β-hydroxy-4'-deoxyleurosidine, the epimeric alcohol. The 3'-ketone can also be epimerized to yield a 4'-ethyl derivative belonging to the 4'-deoxy VLB (or deoxy VLB "A") series. Reduction of this epimeric ketone yields both 3'β-hydroxy-4'-deoxy VLB and, in smaller quantities, 3'α-hydroxy-4'-deoxy VLB.

The acylates of this invention are prepared from any of the above 3'-hydroxy compounds utilizing standard procedures; i.e., use of an anhydride in the presence of a tertiary amine base. Carbamates are prepared by reaction of the alcohol with an alkyl isocyanate. The C-3 amides, hydrazides and the like are prepared by the method of Belgian Pat. No. 837,390. Compounds belonging to the vincristine series or 1-formylleurosidine series (compounds according to formula II above in which $R^2$ is CHO) are prepared by the low temperature chromic acid oxidation of the corresponding compound in which $R^2$ is methyl in the VLB or leurosidine series using the procedure of U.S. Pat. No. 3,899,493.

It is not immediately apparent why Neuss, Gorman, Cone, and Huckstep *Tetrahedron Letters*, 783 (1968) did not find any 3'-hydroxy-4'-deoxyleurosidine when they reacted leurosine with Raney nickel in anhydrous ethanol. The sole difference, as far as can be seen, between the process of this invention and that of Neuss, et al., is the use of prehydrogenated Raney nickel of activity $W^4$ rather than Raney nickel of activity $W^1$ by Neuss et al. Yields of 3'-hydroxy-4'-deoxyleurosidine have been 10 to 20 percent using the more active Raney nickel and this quantity of compound is too large to have been "missed" during the previous reaction by Neuss, et al., using the less active Raney nickel. It can only be assumed that the less active Raney nickel gave far less quantity, if any, of 3'-hydroxy derivative and that, if the compound was present at all, it was in an amount that could not be detected.

This invention is further illustrated by the following specific examples:

EXAMPLE 1

PREPARATION OF 3'α-HYDROXY-4'-DEOXYLEUROSIDINE

A suspension of 10.0 g. of highly purified leurosine in 700 ml. of 95 percent ethanol was placed in a 1 l. 3-neck round bottom flask fitted with stopper, mechanical stirrer and condenser. About 16 g. of activity W-4 Raney nickel were added, and the reaction mixture was heated at reflux with stirring for about 1 hour, at the end of which time thin-layer chromatography (using a 1:1:1 methylene chloride/ethyl acetate/ethanol system) indicated that there was no leurosine remaining and that there were two poorly resolved products present having a low $R_f$. The reaction mixture was cooled and filtered. The catalyst was washed with 95 percent ethanol. The solvent was removed from the filtrate by evaporation to a volume of about 150 ml. The resulting mixture was redissolved by heating. Additional ethanol to a total volume of 300 ml. was added and the solution was allowed to crystallize. The crystalline material was predominantly deoxy VLB "B" (4'-deoxyleurosidine). The mother liquor was concentrated in vacuo to give 4.5 g. of a residue which was chromatographed over 250 g. of silica gel (Woelm activity I) as follows: the residue was placed on the column in methylene dichloride solution. The chromatogram was developed with a 20:1:1 diethyl ether/toluene/diethyl amine solvent mixture containing increasing amounts of methanol (from 1.8 to 45 percent). The first 1.75 l. of eluate were discarded. The next 100 ml. yielded 468 mg. of substantially pure 3'α-hydroxy-4'-deoxyleurosidine contaminated with a small amount (<5 percent) of the corresponding 6,7-dihydro derivative. The next 200 ml. of eluate yielded 648 mg. of very pure 3'α-hydroxy-4'-deoxyleurosidine. The compound had the following physical characteristics: $pK_a$: (66% DMF) 8.19, 5.17; ultra violet spectrum: $\lambda_{max}^{EtOH} = 215$ ($\epsilon 4.51 \times 10^4$), 263, 288, 297 nm; infrared spectrum: $\nu^{CHCl_3} = 3450$, 1730, 1230 cm$^{-1}$; rotation: $[\alpha]_D^{25} = +7.1°$ (CH$_3$OH); mass spectrograph: m/e 810, 751, 469, 355, 282, 154; 100 megaHertz proton magnetic resonance spectrum: $\delta_{TMS}^{CDCl_3}$ 7.95 (brs, 1H, indole N-H), 7.38–7.57 (m, 1H, H$_{11}$); 7.0–7.2 (m, 3H, H$_{12,13',14'}$); 6.52 (s, 1H, H$_{14}$); 6.09 (s, 1H, H$_{17}$); 5.74–5.95 (brdd, J = 4, 10, 1H, H$_7$); 5.45 (s, 1H, H$_4$); 5.30, (brd, J = 10, 1H, H$_6$); 3.79 and 3.80 (2s, 6H, C-24 and -25 methyls); 3.75 (s, 1H, H$_2$); 3.59 (s, 3H, C-18' CO$_2$CH$_3$); 2.69 (s, 3H, N-CH$_3$); 2.65 (s, 1H, H$_{19}$); 2.07 (s, 3H, CH$_3$CO$_2$); 0.80 and 0.95 (2t, J = 7.3, 6H, C-21 and -21' methyls).

The sulfate of 3'α-hydroxy-4'-deoxyleurosidine was prepared by dissolving 695 mg. of the base in 5 ml. of anhydrous ethanol and adding 2.38 ml. of 2 percent ethanolic sulfuric acid (volume/volume). An immediate precipitate of the sulfate salt formed which was separated by filtration. The filter cake was washed with ethanol to give a yield of 666 mg. of a fluffy white solid consisting of 3'α-hydroxy-4'-deoxyleurosidine sulfate.

EXAMPLE 2

PREPARATION OF 3'-OXO-4'-DEOXYLEUROSIDINE

A mixture of 494 mg. of N-chlorosuccinimide and 10 ml. of anhydrous toluene was stirred magnetically for five to 10 minutes at ambient temperature in a 25 ml. three-neck round-bottom flask fitted with stopper, serum cap, and gas inlet tube. The mixture was then cooled to about 0° C. and 345 mg. of dimethylsulfide were added. This new mixture was stirred at about 0° C. for 30 minutes. Next, a solution containing 500 mg. of 3'α-hydroxy-4'-deoxyleurosidine in 2.5 ml. of methylene dichloride was added by pipette. An additional 1.5 ml. of methylene dichloride was used to wash the solution from the pipette. This new reaction mixture stirred at 0° C. under a nitrogen atmosphere for 6 hours. Next, 375 mg of triethylamine were added and the mixture stirred at ambient temperature for about 30 minutes. More methylene dichloride was added and the organic solution washed with water. The aqueous layer was separated and extracted twice more with methylene dichloride. The methylene dichloride layers were combined, dried, and concentrated in vacuo to a residual thick yellow oil. TLC showed no material present in the thick oil corresponding to starting material. The oily residue was chromatographed over 20 g. of silica gel (Woelm activity I). The compound was applied with a 1:1 methylene dichloride/ethyl acetate solvent mixture containing 2 percent methanol. Elution was carried out with the same solvent mixture containing, in 150 ml. fractions, increasing amounts of methanol from 2 to 6 percent. The first 10 fractions collected were of 20 ml. volume and the remaining 10 ml. volume. Fractions 18–25 contained a single material by TLC, consisting of 108 mg. of 3'-oxo-4'-deoxyleurosidine having the following physical characteristics: ultra violet spectrum: $\lambda_{max}^{EtOH} = 215$ ($\epsilon 4.73 \times 10^4$), 265, 287, 296 nm; infrared spectrum: $\nu^{CHCl_3}$ 3460, 1735, 1720, 1230 cm$^{-1}$; mass spectrograph: m/e 808, 749, 649, 282, 152; 100 megaHertz proton magnetic resonance spectrum: $\delta_{TMS}^{COCl_3}$ 8.01 (brs, 1H, indole N-H); 7.45–7.63 (m, 1H, C(11')-H); 7.05–7.25 (m, 3H, C(12'–14')-H); 6.52 (s, 1H, C(14)-H); 6.12 (s, 1H, C(17)-H); 5.75–5.95 (brdd, J = 4 and 10; 1H, C(7)-H); 5.45 (s, 1H, C(4)-H); 5.29 (brd, 1H, C(6)-H); 3.84 and 3.78 (2s, 6H, C(24,25)-CH$_3$); 3.73 (s, 1H, C(2)-H); 3.60 (s, 3H, C(18')-CO$_2$CH$_3$); 2.75 (s, 3H, N-CH$_3$); 2.64 (s, 1H, C(19)-2); 2.08 (s, 3H, CH$_3$CO$_2$); 0.81 and 0.92, (2t, J = 7.3, 6H, C(21,21')—CH$_3$).

The sulfate salt was prepared from a solution of the free base in ethanol using 2 percent ethanolic sulfuric acid.

EXAMPLE 3

PREPARATION OF 3'β-HYDROXY-4'-DEOXYLEUROSIDINE

A solution containing about 12 mg. of sodium borohydride in 1 ml. of anhydrous ethanol was stirred magnetically at ambient temperature for several minutes and then cooled to about −20° C. A second solution containing about 15 mg. of 3'-oxo-4'-deoxyleurosidine dissolved in 1 ml. of ethanol was added thereto in dropwise fashion. TLC run 15 minutes after the addition had been completed indicated substantial reduction of the oxo group. The stirring was continued for another 25 minutes at about −20° C. and for 20 minutes while warming from −20° C. to ambient temperature. Chloroform was added and the resulting organic layer separated. The organic layer was washed three times with water by decantation. The organic layer was dried and the solvent removed therefrom to yield 19 mg. of a white solid residue. TLC indicated about 70 percent reduction of the starting 3'-oxo compound.

The above reaction was repeated using 159 mg. of the 3'-oxo compound in 2.5 ml. of ethanol. An additional 1.5 ml. were used to wash in remaining ketone. A 2 ml. volume of ethanol was used to suspend the borohydride. The reaction mixture was cooled only to 0° C. and the reaction stirred at that temperature for about 1.3 hours. At this point in time, TLC showed the reaction to be 80–90 percent complete. After an additional hour of stirring, the TLC spot corresponding to starting material had virtually disappeared. The reaction mixture was then worked up as before and the white solid residue chromatographed over silica gel using a 1:1 methylene dichloride/ethyl acetate solvent mixture containing increasing amounts of methanol. Fractions shown by TLC to contain 3'β-hydroxy-4'-deoxyleurosidine formed in the above reaction were combined to yield 102.5 mg. of crystalline material. The compound thus prepared had the following physical characteristics: infrared spectrum: $\nu^{CHCl_3}$ 3460, 1735, 1230 cm$^{-1}$; pKa: (66% DMF) 8.1, 4.9; ultraviolet spectrum: $\lambda_{max}^{EtOH}$ 215 ($\epsilon$ 4.72 × 10$^4$), 260, 288, 296 nm; mass spectrograph: m/e 810, 779, 751, 469, 355, 282, 154; 100 megaHertz proton magnetic resonance spectrum: $\delta_{TMS}^{CDCl_3}$ 9.74 (brs, 1H, C(3)-O$\underline{H}$); 8.04 (brs, 1H, indole N-$\underline{H}$); 7.42–7.60 (m, 1H, C(11')-H); 7.03–7.23 (m, 3H, C(12'-1-4')-H); 6.59 (s, 1H, C(14)-H); 6.12 (s, 1H, C(17)-H); 5.74–5.96 (brdd, J = 4 and 10, 1H, C(7)-H); 5.48 (s, 1H, C(4)-H); 5.29 (brd, J = 10, 1H, C(6)-H); 3.79 and 3.80 (2s, 6H, C(24, 25)-CH$_3$); 3.74 (s, 1H, C(2)-H); 3.60 (s, 3H, C(18')-CO$_2$C$\underline{H}_3$); 2.70 (s, 3H, N-C$\underline{H}_3$); 2.65 (s, 1H, C(19)-H); 2.09 (s, 3H, C$\underline{H}_3$CO$_2$); 0.81 and 0.96 (2t, J = 7.3, 6H, C(21, 21')-CH$_3$.

The sulfate salt was prepared with 2 percent ethanolic sulfuric acid as previously.

EXAMPLE 4

PREPARATION OF 3'-OXO-4'-DEOXY VLB

A solution was prepared containing 400 mg. of 3'-oxo-4'-deoxyleurosidine in 10 ml. of methanol. The solution was placed in a 50 ml. round-bottom flask and the flask and contents cooled to about 0° C. in an ice bath. 10 ml. of dimethylamine were added. The flask was stoppered, and the reaction stirred at room temperature for 6 hours using a magnetic stirrer. Thin-layer chromatography using a 1:1:1 ethyl acetate/methylene dichloride/methanol solvent system indicated about 50 percent completion of the reaction. The solvent and dimethylamine were removed by evaporation in vacuo. The residue was chromatographed over 50 g. of Woelm activity 1 silica gel. The residue was applied to the column using a 1:1 ethyl acetate/methylene chloride solvent mixture containing 1 percent methanol. 100 ml. eluant fractions were used with a 1:1 ethyl acetate/methylene chloride solvent system containing successively 1, 2, 3, 4, 5, 7, 10 and 15 percent methanol respectively followed by 200 ml. of 20 percent methanol in the same solvent system. 15 ml. eluate fractions were collected. Fractions 17–34 were combined to yield 114 mg. of a white crystalline residue comprising 3'-oxo-4'-deoxy VLB formed in the above reaction. Fractions 43–60 were combined to yield 168 mg. of starting material. 3-oxo-4'-deoxy VLB thus prepared had the following physical characteristics: mass spectrograph: m/e 808, 749, 649, 152; 100 megaHertz proton magnetic resonance spectrum: $\delta_{TMS}^{CDCl_3}$ 8.04 (brs, 1H, indole N-H); 7.46–7.61 (m, 1H, C(11')-H); 7.03–7.28 (m, 3H, C(12'–14')-H); 6.57 (s, 1H, C(14)-H); 6.11 (s, 1H, C(17)-H); 5.75–5.95 (brdd, J = 4 and 10, 1H, C(7)-H); 5.46 (s, 1H, C(4)-H); 5.31 (brd, J = 10, 1H, C(6)-H); 3.79 (s, 6H, C(24, 25)-CH$_3$); 3.74 (s, 1H, C(2)-H); 3.61 (s, 3H, C(18')-CO$_2$CH$_3$; 2.72 (s, 3H, N-CH$_3$); 2.66 (s, 1H, C(19)-H); 2.09 (s, 3H, CH$_3$CO$_2$); 0.93 and 0.81 (2t, J = 7.3, 6H, C(21,21')-CH$_3$).

EXAMPLE 5

PREPARATION OF 3'β-HYDROXY-4'-DEOXY VLB AND 3'α-HYDROXY-4'-DEOXY VLB

A mixture of 100 mg. of sodium borohydride and 3 ml. of anhydrous ethanol were placed in a 25 ml. flask and the flask and its contents were cooled to 0° C. in an ice bath. A solution of 200 mg. of 3'-oxo-4'-deoxy VLB in 5 ml. of anhydrous ethanol was added thereto in dropwise fashion. The reaction mixture was stirred at 0° C. for about 1.5 hours. Thin-layer chromatography using a 1:1:1 ethyl acetate/methylene chloride/methanol solvent system indicated the presence of a new material of high R$_f$ and a trace of starting material. Another 50 mg. of borohydride were added and the reaction stirred for an additional 1.5 hours. 8 ml. of anhydrous methanol were added and the reaction mixture stored overnight at 0° C. The reaction mixture was then warmed to ambient temperature and stirred at that temperature for about one hour. About 10 ml. each of water and methylene chloride were added. The methylene chloride layer was separated and the aqueous layer was extracted twice with methylene chloride. The methylene chloride layers were combined, washed once with water, and then dried. Removal of the methylene chloride in vacuo yielded 176 mg. of a white residue. The residue was chromatographed over 19 g. of silica gel (Woelm activity I). The residue was applied to the column in a 1:1 methylene chloride/ethyl acetate solvent system containing 2 percent methanol. The chromotogram was developed with 75 ml. portions of the same solvent mixture containing 2, 3, 4, 5, 7, 10, and 15 percent successively of methanol. 15 ml. fractions were collected. Fractions 12–27 were combined to yield 116 mg. of 3'β-hydroxy-4'-deoxy VLB having the following physical characteristics: pK'a: (66% DMF) 7.10, 5.10; ultra violet spectrum: $\lambda_{max}^{EtOH}$ 215 (4.32 × 10$^4$), 260, 288, 296 nm; infrared spectrum: $\nu^{CHCl_3}$ 3450, 1734, 1230 cm$^{-1}$; mass spectrograph: m/e 810, 779, 751, 651, 469, 282, 154; 100 megaHertz proton magentic resonance spectrum: $\delta_{TMS}^{CDCl_3}$ 8.05 (brs, 1H, indole N-H); 7.42–7.59 (m, 1H, C(11')-H); 7.00–7.24 (m, 3H, C(12'-14')-H; 6.64 (s, 1H, C(14)-H); 6.12 (s, 1H, C(17)-H); 5.75–5.95 (brdd, J = 4 and 10, 1H, C(7)-H); 5.47 (s, 1H, C(4)-H); 5.30 (brd, J = 10, 1H, C(6)-H); 3.78–3.79 (2s, 6H, C(24, 25)-CH$_3$; 3.73 (s, 1H, C(2)-H); 3.60 (s, 3H, C(18')-CO$_2$CH$_3$); 2.70 (s, 3H, N-CH$_3$); 2.65 (s, 1H, C(19)-H); 2.09 (s, 3H, CH$_3$CO$_2$; 0.70–1.00 (m, 6H, C(21, 21')-CH$_3$).

Fractions 33–40 were combined, and after evaporation in vacuo, yielded 16 mg. of 3'α-hydroxy-4'-deoxy VLB. The compound had the following physical characteristics: mass spectrograph: m/e 810, 779, 751, 651, 469, 355, 282, 154; 100 megaHertz proton magnetic resonance spectrum: $\delta_{TMS}^{CDCl_3}$ 8.06 (brs, 1H, indole N-H); 7.43–7.59 (m, 1H, C(11')-H); 7.08–7.23 (m, 3H, C(12'-14')-H; 6.57 (s, 1H, C(14)-H); 6.10 (s, 1H, C(17)-H); 5.75–5.97 (brdd, J = 4 and 10, 1H, C(7)-H); 5.47 (s, 1H, C(4)-H); 5.31 (brd, J = 10, 1H, C(6)-H); 3.81 (s, 6H, C(24, 25)-CH$_3$); 3.75 (s, 1H, C(2)-H); 3.64 (s, 3H, C(18')-CO$_2$CH$_3$); 2.73 (s, 3H, N-CH$_3$); 2.65 (s, 1H, C(19)-H); 2.10 (s, 3H, CH$_3$CO$_2$; 0.81 and 0.98, (2t, J = 7.3, 6H, C(21, 21')-CH$_3$).

EXAMPLE 6

PREPARATION OF 3'α-ACETOXY-4'-DEOXYLEUROSIDINE

About 100 mg. of 3'α-hydroxy-4'-deoxyleurosidine and 30.4 mg. of p-dimethylaminopyridine were dissolved in 2 ml. of methylene dichloride. .94 mcl. of acetic anhydride were added and the reaction mixture stirred at ambient temperature for about 2 hours. The reaction mixture was then diluted with methylene dichloride. Water was next added. The organic phase was separated and washed twice with aqueous sodium bicarbonate. The aqueous layer was made basic and the alkaline layer then extracted twice with methylene dichloride. All methylene dichloride layers and extracts were combined and dried. Evaporation of the solvent yielded 104 mg. of a residue comprising 3'α-acetoxy-4'-deoxyleurosidine. The residue was purified by chromatography over 10 g. of silica gel of Woelm activity I using a 1:1 ethyl acetate/methylene chloride solvent mixture as an eluant containing gradually increasing amounts of methanol (from 2–20 percent) in each 50 ml. portions. Fractions of 10 ml. each were collected. Fractions 19 to 32 were combined to yield 54 mg. of purified 3'α-acetoxy-4'-deoxyleurosidine. The compound showed both a mass spectrum and nuclear magnetic resonance spectrum consistent with the proposed structure. 3'β-acetoxy-4'-deoxyleurosidine, and 3'β-acetoxy-4'-deoxy VLB were prepared in similar fashion. The mass spectra and nuclear magnetic resonance spectrum were consistent with the proposed structure.

EXAMPLE 7

PREPARATION OF 3'α-MESYLOXY-4'-DEOXYLEUROSIDINE

About 200 mg. of 3'α-hydroxy-4'-deoxyleurosidine were dissolved in 4 ml. of pyridine, and the resulting solution cooled to about 0° C. 0.106 ml. (157 mg.) of mesyl chloride (methanesulfonyl chloride) were added in dropwise fashion with a micro syringe to the stirred solution. After the addition had been completed, the reaction mixture was stirred for an additional hour and was then quenched by the addition of ice. Methylene dichloride and water were added. The methylene dichloride layer was separated and washed twice with water. The solvents were removed in vacuo. Benzene was then added and the solvent again removed in vacuo. Thin-layer chromatography using a 2:2:1 benzene/chloroform/methanol solvent system showed no remaining starting material, but two products. The residue thus obtained was purified by chromatography over Woelm activity I silica gel. The faster running material was collected in several fractions and fractions combined. The removal of the solvent and conversion of the residue to the corresponding sulfate salt yielded 53.4 mg. of 3'α-mesyloxy-4'-deoxyleurosidine sulfate.

EXAMPLE 8

PREPARATION OF 3'α-(N-METHYL CARBAMOYLOXY)-4'-DEOXYLEUROSIDINE

A solution was prepared containing 90 mg. of 3'α-hydroxy-4'-deoxyleurosidine in 0.5 ml. of benzene. 0.10 ml. of methyl isocyanate was added dropwise with stirring. The reaction mixture was slowly heated to about 40° C. The reaction mixture was heated for about 2 and one-half hours and then allowed to stand overnight at room temperature. The course of the reaction was followed by thin-layer chromatography. An extra 0.05 ml. of methyl isocyanate was added and the reaction mixture again heated to about 40° C. for about 2 hours. The reaction mixture was evaporated to dryness to yield 57.3 mg. of a residue comprising starting material and 3'α-(methyl carbamoyloxy)-4'-deoxyleusoridine. Chromatography of the residue over Woelm activity I silica gel was carried out using 1:1 benzene/chloroform containing increasing amounts of methanol. Fractions containing the product, are shown by thin-layer chromatography to be different from starting material, were combined and evaporated to yeild 48 mg. of compound of 3'α-(N-methyl carbamoyloxy)-4'-deoxyleurosidine. Rechromatography of the product over silica gel using a 20:1:1 ether/diethylamine/toluene solvent system with increasing amounts of methanol (from 0.5–15 percent) yielded purified 3'α-(N-methyl carbamoyloxy)-4'-deoxyleurosidine. A sulfate salt was prepared using 2 percent ethanolic sulfuric acid.

EXAMPLE 9

PREPARATION OF 4-DESACETYL-3'α-HYDROXY-4'-DEOXYLEUROSIDINE C-3 CARBOXHYDRAZIDE

A solution was prepared from 300 mg. of 3'α-hydroxy-4'-deoxyleurosidine in 9 ml. of anhydrous methanol. 6 ml. of 97 percent hydrazine were added and the reaction vessel flushed with nitrogen and sealed. The reaction mixture was heated over the weekend at about 65° C. Evaporation of the contents to dryness and extraction of the residue twice with ethanol removed any residual hydrazine. Thin-layer chromatography indicated a 2 spot material. The compound was purified by chromatography over Woelm activity I silica gel using a 2:1 benzene/chloroform solvent mixture as an eluant containing 1 percent triethylamine and increasing quantities of methanol. Fractions shown by thin-layer chromatography to contain 4-desacetyl-3'α-hydroxy-4'-deoxyleurosidine C-3 carboxhydrazide were combined. Mass spectrographic nuclear magnetic resonance and infra-red spectrum were consistent with the proposed structure. The hydrazide was converted to the azide using the method of Belgian Pat. No.

837,390 and the azide reacted with methyl amine to yield 4-desacetyl-3'α-hydroxy-4'-deoxyleurosidine C-3 N-methyl carboxamide.

The N-ethyl, N-propyl, N-(β-hydroxy ethyl), N-(β-methoxyethyl), N-(β-mercaptoethyl), N-(β-methylmercaptoethyl) and similar amides of the corresponding 4-desacetyl-3'α-hydroxy-4'-deoxyleurosidine, 4-desacetyl-3'β-hydroxy-4'-deoxyleurosidine, 4-desacetyl-3'α-hydroxy-4'-deoxy-1-formylleurosidine, 4-desacetyl-3'α-hydroxy-4'-deoxy VLB, 4-desacetyl-3'β-hydroxy-4'deoxy VLB, 4-desacetyl-3'α-hydroxy-4'-deoxyvincristine, 4-desacetyl-3'β-hydroxy-4'-deoxyvincristine, the acylates and mesylates, etc. thereof, 4-desacetyl-3'-keto-4'-deoxyleurosidine, 4-desacetyl-3'-oxo-4'-deoxy VLB, 4-desacetyl-3'oxo-4'-deoxy-1-formylleurosidine and 4-desacetyl-3'oxo-4'-deoxyvincristine are all prepared in analogous fashion.

The primary amide of each of the above compounds can be prepared in one of two ways; either the azide can be reacted with ammonia or the hydrazide itself can be hydrogenalized with Raney nickel following the procedure of Ainsworth, U.S. Pat. No. 2,756,235.

EXAMPLE 10

PREPARATION OF 3'α-HYDROXY-4'-DEOXY-1-DESMETHYL-1-FORMYLLEUROSIDINE 203 mg. of 3'α-hydroxy-4'-deoxyleurosidine were dissolved in acetone. About 0.12 ml. of a 2.2 M aqueous sulfuric acid (prepared by diluting 2.5 ml. of 18 M sulfuric acid with 19.9 ml. of water), were added. The solution was cooled to about $-50°$ C. A second solution containing 225 mg. of chromium trioxide in 2.5 ml. of acetic acid and 0.25 ml. of water was added in dropwise fashion over a 5 minute period with magnetic stirring. A dark, apparently homogenous, reaction mixture was obtained. The reaction mixture was stirred at $-50°$ C. for another 20 minutes and was then carefully cooled to $-65°$ C., at which temperature 5 ml. of 14 N aqueous ammonium hydroxide was added. The resulting mixture was poured into a 125 ml. mixture of ice and water. The resulting aqueous layer was extracted three times with chloroform. The organic extracts were combined, washed with dilute aqueous sodium bisulfite and dried. Concentration in vacuo of the organic solution yielded 190 mg. of a greenish solid. Thin-layer chromatography not only lacked a spot corresponding to that expected for the starting alcohol but also showed a new major spot. The greenish residue was therefore chromatographed over 20 g. of silica. The chromatogram was developed with 30 ml. portions of 2:1 benzene/chloroform solvent mixture containing successively 6, 9, 13.5, 20, 30, and 45 percent methanol. 10 ml. fractions were collected. Fractions 14-22 were combined and yielded, after evaporation of the solvent, 131 mg. of a light green solid, 3'α-hydroxy-4'-deoxy-1-desmethyl-1-formylleurosidine formed in the above reaction. The compound was one spot material by thin-layer chromatography and had the following physical characteristics: infrared spectrum (in chloroform): peaks at 3480, 1746, 1692 and 1220 cm$^{-1}$; ultra violet spectrum: $\lambda_{max.}^{EtOH} = 215$ ($\epsilon = 3.75 \times 10^4$), 222, 256, 298 nm; nmr: $\delta_{TMS}^{CDCl_3}$ 8.79 (CHO), 8.03 (indole NH); no peak for NCH$_3$.

The compound was converted to the corresponding sulfate salt with 2 percent (v/v) ethanolic sulfuric acid.

During the preparation of the hydrazide derivatives of the 3'-oxygenated derivatives of 4'-deoxyleurosidine and 4'-deoxy VLB, as well as of the corresponding 1-formyl compounds, the hydrazine-azide-amide reaction sequence outlined above usually results in the formation of a 4-desacetyl derivative in that the acetyl group originally present at C-4 is hydrolyzed during one or more of these reactions. Most of these 4-desacetyl amides can be reacylated with an aliphatic anhydride or acid chloride to yield the corresponding C-4 acetate in accordance with the procedure of U.S. Pat. No. 3,392,173.

EXAMPLE 11

PREPARATION OF SALTS

Other salts, including salts with inorganic anions such as chloride, bromide, phosphate, nitrate and the like as well as salts with organic anions such as acetate, chloroacetate, trichloroacetate, benzoate, alkyl or aryl sulfonates and the like, are prepared from the compounds of this invention by a procedure analogous to that set forth in Example 1 above for the preparation of the sulfate salt by substituting the appropriate acid in a suitable diluent in place of the 2 percent ethanolic sulfuric acid of that example.

The compounds of this invention are active against transplanted tumors in mice in vivo and induce metaphase arrest in Chinese hamster ovary cells maintained in tissue culture in a procedure adapted from that of Siminoff, *Applied Microbiology*, 9, 66-72 (1961).

In demonstrating activity of the drugs of this invention against transplanted tumors in mice, a protocol was used which involved the administration of the drug, usually by the intraperitoneal route, at a given dose level for 3-10 days after innoculation with the tumor.

The following table — Table 1 — gives the results of several experiments in which mice bearing transplanted tumors were treated successfully with a compound of this invention. In the table, column 1 gives the name of the compound; column 2, the abbreviation of the name of transplanted tumor; column 3, the dose level and the number of days that dosage was administered; column 4, the evaluation day after any administration; and column 5, the percent inhibition of tumor growth or percent prolongation of survival time. (GLS is an abbreviation for Gardner lymphosarcoma B16 is a melanoma, P388 is a leukemia; and WA-256 ASCITES is the ascites form of Walker rat carcinoma 256.)

In utilizing the novel compound of this invention as anti-tumor agents in mammals, the parenteral route of administration is conveniently employed. With parenteral administration, the intravenous route is preferred although with smaller mammals such as mice the intraperitoneal route may be used. For parenteral administration, isotonic solutions are employed containing 1-10 mg./ml. of a salt of the alkaloidal base formula II. The compounds are administered at a rate of from 0.01 to 15 mg./kg. and preferably from 0.1 to 1 mg./kg. of mammalian body weight once or twice a week or every two weeks depending on both the activity and the toxicity of the drug. An alternative method of arriving at a therapeutic dose is based on body — surface area with a dose in the range 0.1 to 10 mg./meter squared of mammalain body surface every 7 or 14 days.

TABLE 1

| Compound | Tumor | Dose mg./kg. × Days | Day | Percent Inhibition or Prolongation of Survival Time |
|---|---|---|---|---|
| 3'α-Hydroxy-4'-deoxy-1-desmethyl-1-formyl-leurosidine sulfate | GLS | 12 × 10 | 7 | 100 |
| | | | 11 | 84 |
| | | 6 × 10 | 7 | 94 |
| | | | 11 | 100 |
| | | 3 × 10 | 7 | 93 |
| | | | 11 | 85 |
| | | 1.5 × 10 | 7 | 59 |
| | | | 11 | 51 |
| | | 1.8 × 19 | 8 | 74 |
| | | | 15 | Toxic |
| | | | 22 | Toxic |
| | | | 7 | 67 |
| 3'α-Mesyloxy-4'-deoxy-leurosidine sulfate | GLS | 3.0 × 10 | 11 | 49 |
| | | 1.5 × 10 | 7 | 36 |
| | | 0.75 × 10 | 11 | 15 |
| | | | 7 | 16 |
| | | | 11 | 13 |
| 3'α-Hydroxy-4'-deoxy-leurosidine C-4 carboxhydrazine | GLS | 12 × 10 | 7 | 100 |
| | | | 11 | 85 |
| | | 6 × 10 | 7 | 94 |
| | | | 11 | 100 |
| | | 3 × 10 | 7 | 100 |
| | | | 11 | 87 |
| | | 1.5 × 10 | 7 | 37 |
| | | | 11 | 33 |
| 3'α-Hydroxy-4'-deoxy-leurosidine sulfate | B-16 | 9 × 3 | | 36 |
| | WA-256 | 6 × 10 | | Toxic |
| | Ascites | 3 × 10 | | 5* |
| | | 1.5 × 10 | | 479* |
| | P-388 | 7.5 × 10 | | 102 |
| | | 3.75 × 10 | | 79 |
| 3'-oxo-4'-deoxy-leurosidine sulfate | P-388 | 7.5 × 10 | | 38 |

*4 out of 5 indefinite survivors

We claim:

1. A compound of the formula:

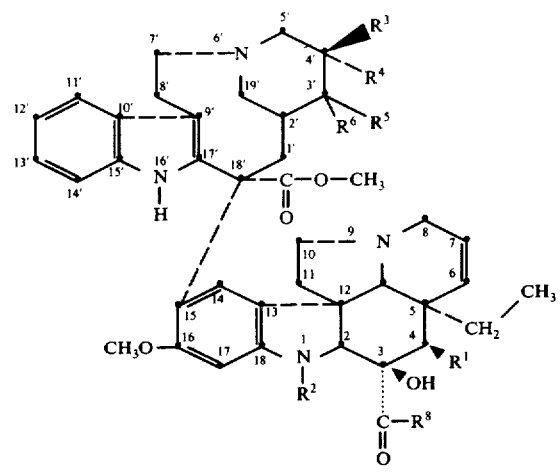

wherein $R^1$ is OH or acetoxy; $R^2$ is $CH_3$ or CHO, one of $R^3$ and $R^4$ is hydrogen and the other is ethyl; when taken singly, one of $R^5$ and $R^6$ is a β-hydrogen and the other is an α-$OR^7$ group and, when taken together, are oxygen; wherein $R^7$ is hydrogen or $$\text{alk}-\text{NH}-\overset{\overset{O}{\|}}{C}, \text{alk}-\overset{\overset{O}{\|}}{C} \text{ or alk}-\overset{\overset{O}{\|}}{\underset{\underset{O}{\|}}{S}};$$

$R^8$ is $OCH_3$, $NH_2$, $NH-CH_3$, $NH-NH_2$, $N_3$, $NH-CH_2-CH_2-OH$, $NH-CH_2-CH_2-O-$alk, $NH-CH_2-CH_2-SH$ or $NH-CH_2-CH_2-S-$alk; and wherein alk is ($C_1-C_3$) alkyl such that, when $R^1$ is acetoxy, $R^8$ is $OCH_3$, $NH_2$, $NH-CH_3$, $NH-CH_2-CH_2-O-$alk or $NH-CH_2-CH_2-S-$alk, and pharmaceutically acceptable acid addition salts thereof.

2. A compound according to claim 1, said compound being 3'-oxo-4'-deoxyleurosidine.

3. The sulfate salt of the compound of claim 2.

4. A compound according to claim 1, said compound being 3'α-hydroxy-4'-deoxy VLB.

5. A compound according to claim 1, said compound being 3'α-hydroxy-4'-deoxyleurosidine.

6. The sulfate salt of the compound of claim 5.

7. A compound according to claim 1, said compound being 3'-oxo-4'-deoxy VLB.

8. A 3'-acetate of a compound according to claim 1 wherein one of $R^5$ and $R^6$ is hydrogen and the other is hydroxyl.